(12) United States Patent
Jack et al.

(10) Patent No.: US 7,127,092 B2
(45) Date of Patent: Oct. 24, 2006

(54) REDUCTION OF MOTION ARTIFACT IN NMR IMAGES USING SPHERICAL NAVIGATOR SIGNALS

(75) Inventors: Clifford R. Jack, Rochester, MN (US); Armando Manduca, Rochester, MN (US); Roger Grimm, Rochester, MN (US); Edward B. Welch, Rochester, MN (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 677 days.

(21) Appl. No.: 10/258,268

(22) PCT Filed: Apr. 16, 2001

(86) PCT No.: PCT/US01/12355

§ 371 (c)(1),
(2), (4) Date: Feb. 4, 2003

(87) PCT Pub. No.: WO01/84173

PCT Pub. Date: Nov. 8, 2001

(65) Prior Publication Data

US 2003/0153826 A1 Aug. 14, 2003

Related U.S. Application Data

(60) Provisional application No. 60/199,854, filed on Apr. 26, 2000, provisional application No. 60/210,929, filed on Jun. 12, 2000.

(51) Int. Cl.
*G06K 9/00* (2006.01)

(52) U.S. Cl. .................... 382/128; 424/9.3; 436/173

(58) Field of Classification Search ........ 382/128–134, 382/275, 294; 600/407, 409, 410, 413, 425, 600/524; 324/300, 307, 309, 312, 314, 318; 430/31, 39; 436/173; 424/9.3
See application file for complete search history.

(56) References Cited

U.S. PATENT DOCUMENTS

| 5,122,747 | A | * | 6/1992 | Riederer et al. ............ 324/309 |
| 5,519,320 | A | * | 5/1996 | Kanayama et al. ......... 324/309 |
| 5,539,312 | A | | 7/1996 | Fu et al. ..................... 324/309 |
| 5,671,739 | A | * | 9/1997 | Darrow et al. .............. 600/424 |
| 6,037,771 | A | * | 3/2000 | Liu et al. .................... 324/309 |
| 6,181,832 | B1 | | 1/2001 | Maas, III .................... 382/294 |
| 6,198,959 | B1 | * | 3/2001 | Wang .......................... 600/413 |
| 6,268,730 | B1 | * | 7/2001 | Du ............................. 324/309 |
| 6,292,684 | B1 | * | 9/2001 | Du et al. ..................... 600/410 |
| 6,411,089 | B1 | * | 6/2002 | Anand et al. ............... 324/309 |

OTHER PUBLICATIONS

Lee C C et al: A prospective approach to correct for inner-image head rotation in FMRI' Magnetic Resonance in Medicine, Academic Press, Duluth, MN, US, vol. 39, No. 2, 1998, pp. 234-243, XP002175905; ISSN: 0740-3194.

(Continued)

*Primary Examiner*—Jingge Wu
*Assistant Examiner*—Abolfazl Tabatabai
(74) *Attorney, Agent, or Firm*—Quarles & Brady LLP (57) ABSTRACT

A series of fMRI image frames are acquired along with interleaved navigator signals. The navigator signals are acquired while three orthogonal readout gradients are applied such that a spherical surface is sampled in k-space. The navigator signals are analyzed to measure subject rotational and translational motion during the scan.

14 Claims, 6 Drawing Sheets

OTHER PUBLICATIONS

Zhuo Wu Fu et al: "Orbital navigator echoes for motion measurements in magnetic resonance imaging", Magnetic Resonance in Medicine, Academic Press, Duluth, MN, US, vol. 34, No. 5, Nov. 1, 1995, pp. 746-753, XP000538745; ISSN: 0740-3194.

* cited by examiner

REDUCTION OF MOTION ARTIFACT IN NMR IMAGES USING SPHERICAL NAVIGATOR SIGNALS

RELATED APPLICATIONS

This application claims benefit of provisional application Ser. Nos. 60/199,854 and 60/210,929 filed in the United States Patent and Trademark Office on Apr. 26, 2000 and Jun. 12, 2000.

STATEMENT REGARDING FEDERALLY SPONSORED RESEARCH

This invention was made with government support under Grant No. NIH CA73691 awarded by the National Institute of Health. The United States Government has certain rights in this invention.

BACKGROUND OF THE INVENTION

The field of the invention is nuclear magnetic resonance imaging methods and systems. More particularly, the invention relates to the reduction of motion artifacts in NMR images using correction methods described in U.S. Pat. No. 4,937,526.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant $\gamma$ of the nucleus). Nuclei which exhibit this phenomena are referred to herein as "spins".

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$, which is rotating, or spinning, in the x-y plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified.

Object motion during the acquisition of NMR image data produces both blurring and "ghosts" in the phase-encoded direction. Ghosts are particularly apparent when the motion is periodic, or nearly so. For most physiological motion each view is acquired in a period short enough that the object may be considered stationary during the acquisition window. In such case the blurring and ghosting is due to the inconsistent appearance of the object from view to view. Motion that changes the appearance between views such as that produced by a patient moving, by the respiration or the cardiac cycle, or by peristalsis, is referred to hereinafter as "view-to-view motion". Motion may also change the amplitude and phase of the NMR signal as it evolves during the pulse sequence and such motion is referred to hereinafter as "in-view motion".

Both blurring and ghosting can be reduced if the data acquisition is synchronized with the functional cycle of the object to reduce view-to-view motion. This method is known as gated NMR scanning, and its objective is to acquire NMR data at the same point during successive functional cycles so that the object "looks" the same in each view. The drawback of gating is that NMR data may be acquired only during a small fraction of the object's functional cycle, and even when the shortest acceptable pulse sequence is employed, the gating technique can significantly lengthen the data acquisition.

U.S. Pat. No. 4,937,526 describes a method for reducing motion artifacts in NMR images in which the NMR data set used to reconstruct the image is corrected after its acquisition using information acquired concurrently in NMR "navigator" signals. The navigator signals are produced by pulse sequences which are interleaved with the imaging pulse sequences and which are characterized by the absence of phase encoding. The navigator signal is thus a projection along an axis defined by the readout gradient which is fixed in direction throughout the scan. As a result, the navigator signals detect spin motion only along the direction of this readout gradient. A second navigator pulse sequence with an orthogonal readout gradient can also be interleaved throughout the scan, but this further lengthens the scan time and is seldom done. In addition, even when two "orthogonal" navigator signals are acquired during the scan, they do not provide the information required to correct for in-plane rotation of the subject. Such rotational motion is particularly troublesome when imaging certain subjects such as the human heart, or when performing brain function MRI.

The difficulty in correcting for rotational motion has been solved as described in U.S. Pat. No. 5,539,312. Navigator signals are acquired using a unique pulse sequence which samples two-dimensional k-space in a circular trajectory. These "orbital" navigator signals are used to correct NMR image data for rotation and translation in a single two-dimensional plane. To obtain sufficient information to correct for all possible rotations and translations, the orbital navigator pulse sequence must be performed three times.

Functional magnetic resonance imaging (fMRI) of the brain is performed by acquiring a time-series of images of one or more anatomic sections of interest. As described, for example, in U.S. Pat. No. 5,603,322, algorithms used to extract functional activity from an fMRI time-series are based on the assumption that signal intensity fluctuations in each voxel are dependent only on physiologic changes induced by a functional activation task of known timing.

However, image-to-image global head motion invalidates this assumption. Motion occurring over the acquisition of the time-series of images can be conceptually divided into two categories: intra-image motion and inter-image motion. Intra-image motion refers to view-to-view motion which occurs during the period of time that the phase-encoded lines of data necessary to reconstruct a single image are being acquired. This motion can originate from i) respiratory expansion and contraction of the thorax, ii) cardiac-driven pulsatility of the brain, overlying vessels, and cerebral spinal fluid, and iii) bulk rotational and translational head motion. Intra-image motion results in image blurring and ghosting. However, for fMRI studies performed with single-shot EPI acquisition in which all data for one image are collected in under 100 msec, intra-image (view-to-view) motion is not a major problem. Inter-image motion is defined as that occurring between acquisition of successive images in an fMRI time-series and arises from global head movement. It cannot be rectified by fast scanning. Virtually every publication to date addressing in vivo fMRI has at some level acknowledged head motion as a fundamental limitation.

SUMMARY OF THE INVENTION

The present invention is a method for detecting translational and rotational motion of the subject being imaged along or about an axis. More specifically, the invention includes acquiring a series of NMR signals using an imaging pulse sequence to acquire image NMR data; interleaving with the series of imaging pulse sequences a series of pulse sequences to acquire a corresponding series of navigator NMR signals, each navigator pulse sequence including the application of three orthogonal magnetic field gradients during the readout of its navigator NMR signal such that the navigator NMR signal samples a substantially "spherical" surface in three-dimensional k-space.

A general object of the invention is to provide information with which an acquired image NMR data set can be corrected for subject motion along or about any axis. By measuring shifts in the spherical navigator NMR signals with respect to a reference spherical navigator signal, corrective values can be calculated for each corresponding NMR imaging signal. These corrections offset artifact producing errors caused by translational motion of spins in any direction, as well as errors caused by rotational motion of spins about any axis.

Another object of the invention is to acquire information from which corrections can be made to an image NMR data set without further lengthening the scan time. A single spherical navigator pulse sequence is sufficient to acquire corrective information for all possible rotational and translational spin motions. It requires substantially the same scan time as prior "single axis" navigator pulse sequences.

Yet another object of the invention is to detect motion of the subject being imaged during an NMR scan. By interleaving navigator pulse sequences into the NMR scan, subject motion can be monitored throughout the acquisition. The detected movement may be used to correct the acquired NMR image data, or it may be used in other ways. For example, detected motion may be employed as a means for gating the acquisition of NMR image data, or it may be used as a signal to discard and reacquire NMR image data, or it may be used to simply stop the NMR scan when the detected motion is unacceptable for the procedure being performed.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

A spherical navigator (SNAV) dataset is formed by acquiring data points which describe a spherical 3D shell in k-space. The SNAV dataset is acquired prior to each set of images in an fMRI time series, prior to each view in a conventional phase-encoded MRI scan, or prior to each block of views in a multi-shot MRI scan. Motion is detected by comparing the current SNAV dataset to its predecessor in time. Rotations of the patient's head are encoded in the magnitude of the SNAV signal and translations are encoded in the phase of the signal. The single SNAV dataset contains information about rotation and translation of the object in all three dimensions.

The degrees of rotational freedom may be expressed as successive rotations about the x, y, z axes in that order. Other ways of expressing 3D rotations exist, but this is a convenient representation and is suitable when the rotation angles are small. In this representation, a point (x, y, z) is mapped from a point (x', y', z') by rotations $\theta_x, \theta_y, \theta_z$ and translations $x_0, y_0, z_0$ by:

$$\begin{bmatrix} x \\ y \\ z \end{bmatrix} = M \begin{bmatrix} x' \\ y' \\ z' \end{bmatrix} + \begin{bmatrix} x_0 \\ y_0 \\ z_0 \end{bmatrix}$$

where $M = \begin{bmatrix} c_y c_z & s_x s_y c_z - c_x s_z & c_x s_y c_z + s_x s_z \\ c_y s_z & s_x s_y s_z - c_x c_z & c_x s_y s_z - s_x c_z \\ -s_y & s_x c_y & c_x c_y \end{bmatrix}$ and where $c_x = \cos(\theta_x)$, $s_y = \sin(\theta_y)$, etc.

In k-space, the same rotation matrix applies, but the translations become phase terms. A signal S' measured at the new location $(k_x, k_y, k_z)$ or $(k\rho, \theta', \phi'$ in polar coordinates) by:

$$S'(k_x, k_y, k_z) = S'(k_\rho, \theta, \phi) = S(k_\rho, \theta', \phi')e^{i2\pi(k_x x_0 + k_y y_0 + k_z z_0)} \quad (1)$$

$$= S(k_\rho, \theta', \phi')e^{i2\pi k_\rho(x_0\cos\theta\cos\phi + y_0\sin\theta\cos\phi + z_0\sin\phi)}.$$

There are no simple direct formulas for $\theta$ and $\phi$ in terms of $\theta'$ and $\phi'$, but they can be deduced from $(k_x, k_y, k_z)$. Notice that $k_\rho$ does not change. Rotations of an object in space correspond to rotations in k-space, in which points simply rotate on a spherical surface and their magnitude values do not change. Translations simply add phase shifts to points in k-space, and thus do not affect the magnitude values. Off-center rotations are equivalent to an on-center rotation plus an apparent translation of the coordinate frame. Also, one should note that in 3D any combination of rotations is equivalent to a single rotation about some axis.

Figure 7A:
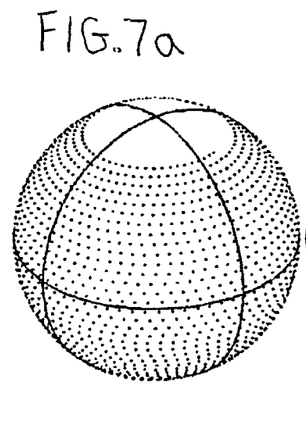
FIGS. 7a–c are pictoral representations of the sampled spherical surface and resulting texture maps.
Figure 7B:
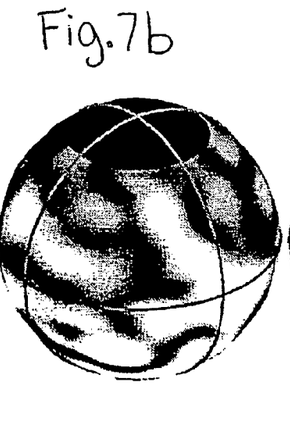
Figure 7C:
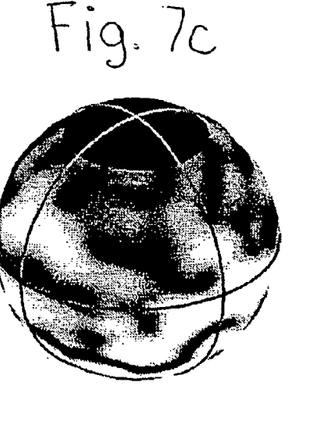

In order to detect a change in rotation of a given SNAV dataset $(SNAV_n)$ with respect to its reference, or baseline $(SNAV_0)$, $SNAV_n$ is rotated about the origin of 3D k-space, and the magnitude values on the surface of $SNAV_n$ are compared with those on the surface of $SNAV_0$ at each new rotational position. The magnitude data on a spherical surface in k-space at an appropriate radius has features. This "intensity texture" of the SNAVs simply rotates with arbitrary 3D rotations, so the patterns before and after a rotation can be matched, or registered, and the rotation parameters that yield the best registration are recorded. This is a registration problem, analogous to rotating the earth's surface in an arbitrary way and deducing the rotation parameters by "lining up" the mountain ranges and valleys. This registration process is straightforward provided that there are sufficient features on the spherical surface and that it is sampled densely enough. FIGS. 7a–c illustrate (from left to right) the bi-hemispheric K-space sampling scheme that is employed in the preferred method; a texture map derived from the $SNAV_0$ data in base-line position; and, a texture map of the same object after a rotation. The great circles are intended to aid visualization of rotation of the texture features with respect to the constant position of the great circles.

Figure 6:
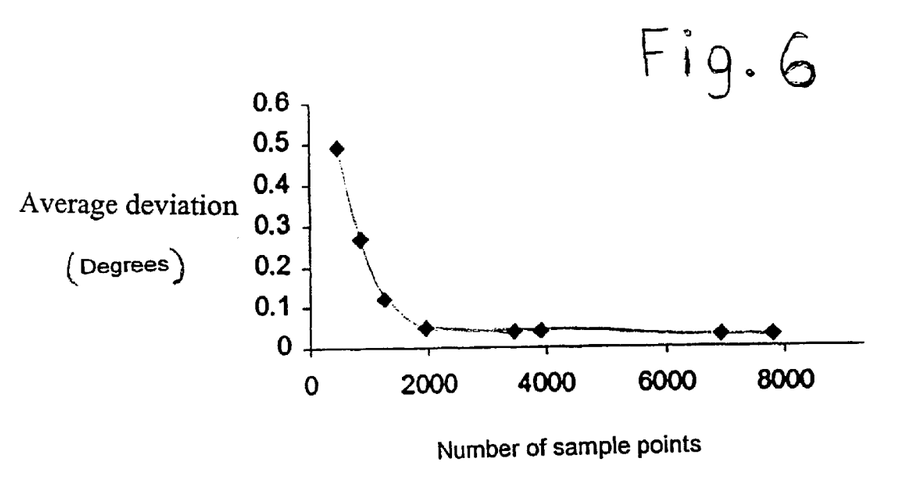
FIG. 6 is a graph showing the reliability of the motion measurement as a function of number of navigator signal samples.

Experiments have been conducted to determine the accuracy of the motion measurements and the minimum number of sample points required to obtain this accuracy. Spherical k-space surfaces were sampled substantially uniformly at different densities and used to measure rotation of a phantom. FIG. 6 is a graph which shows the deviation of the measured phantom rotation using progressively smaller numbers of k-space samples. It was discovered that the measurements do not deviate significantly until less than 1000 samples are acquired. The optimal number of samples of the k-space spherical surface is in the range of 1000 to 2000 samples. This is significant in that this number of samples can be obtained during a single pulse sequence. The precision of the method is within ±0.1° for all axes when 1952 samples of the k-space surface are acquired.

Experiments have also been conducted to determine the dynamic range of the SNAV measurements and their sensitivity. These measurements indicate that movements up to ±5° of rotation and up to ±5 mm of translation can be measured, and that the measurements have submillimeter and subdegree accuracy. The accuracy of motion detection is substantially equivalent to prior navigator signal measurement methods.

Another variable in the SNAV method is the radius $k_\rho$ of the spherical surface. The SNR of acquired SNAV signals is proportional to $k_\rho^{-1/2}$ with the result that increased spherical radius decreases the SNAV signal-to-noise ratio. However, a larger radius $k_\rho$ increases the spatial detail in the sampled subject resulting in a more accurate registration of the acquired $SNAV_n$ and the reference $SNAV_0$. The radius $k_\rho$ is limited by the maximum gradient slew rates on the MRI system. At maximum gradient slew rates, $k_\rho$ is inversely proportional to the number of turns on the spherical surface. The radius $k_\rho$ used in the preferred embodiment is 9.5.

DESCRIPTION OF THE PREFERRED EMBODIMENT

Figure 1:
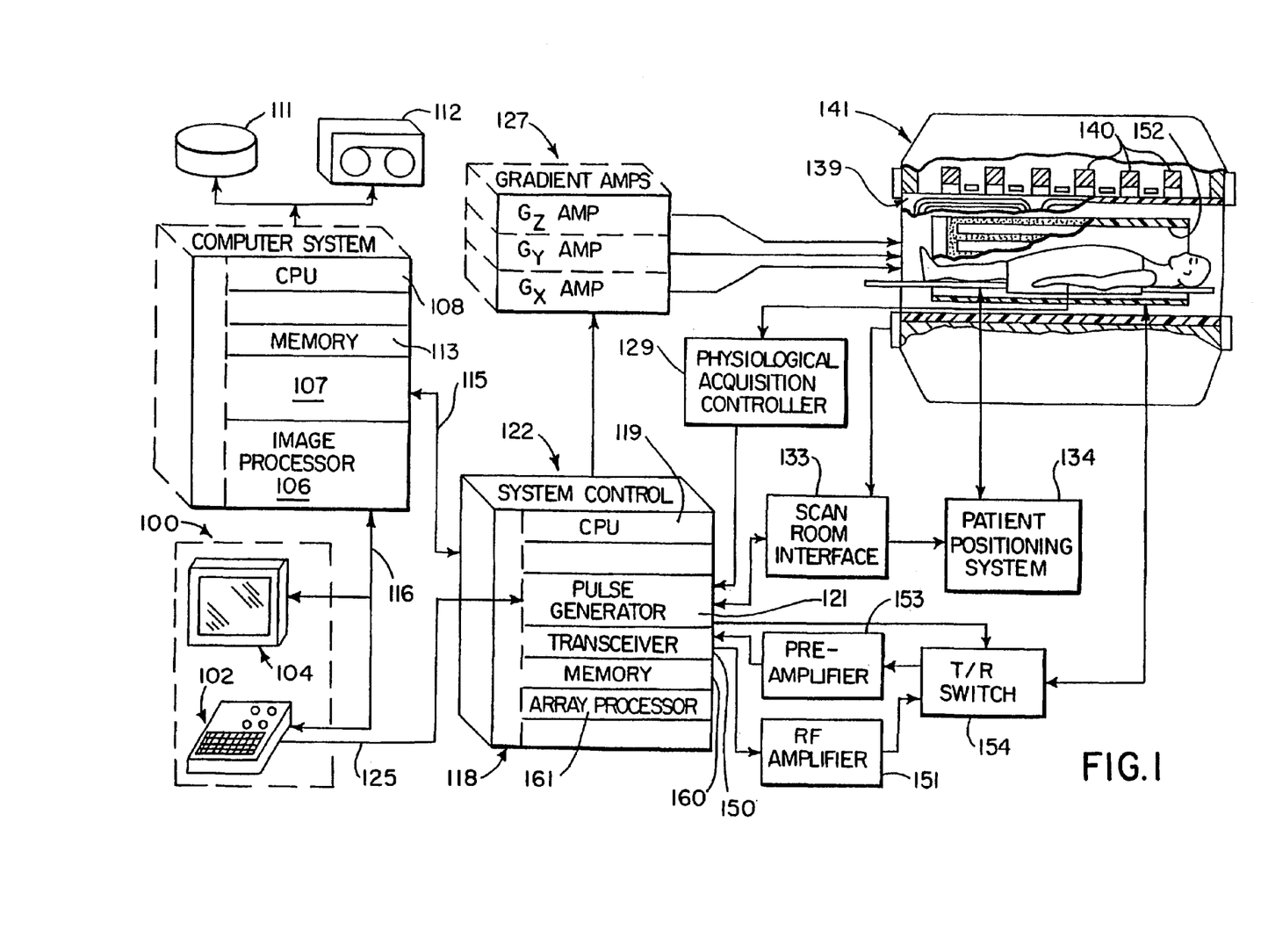
FIG. 1 is a block diagram of an NMR system which has been modified to practice the present invention.

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 includes a number of modules which communicate with each other through a backplane. In addition to the application interface 117 and the image processor 106, these include a CPU module 108 that controls the backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$, and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 141 which includes a polarizing magnet 140 that produces either a 0.5 or a 1.5 Tesla polarizing field that extends horizontally through a bore 142. The gradient coils 139 encircle the bore 142, and when energized, they generate magnetic fields in the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_0$, and the total magnetic field in the z direction is referred to as $B_z$, then $G_x = \partial B_z / \partial x$, $G_y = \partial B_z / \partial y$ and $G_z = \partial B_z / \partial z$, and the magnetic field at any point (x,y,z) in the bore of the magnet assembly 141 is given by $B(x,y,z) = B_0 + G_x x + G_y y + G_z z$. The gradient magnetic fields are utilized to encode spatial information into the NMR signals emanating from the patient being scanned.

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

In addition to supporting the polarizing magnet 140 and the gradient coils 139 and RF coil 152, the main magnet assembly 141 also supports a set of shim coil 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil 152 are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118.

Figure 2:
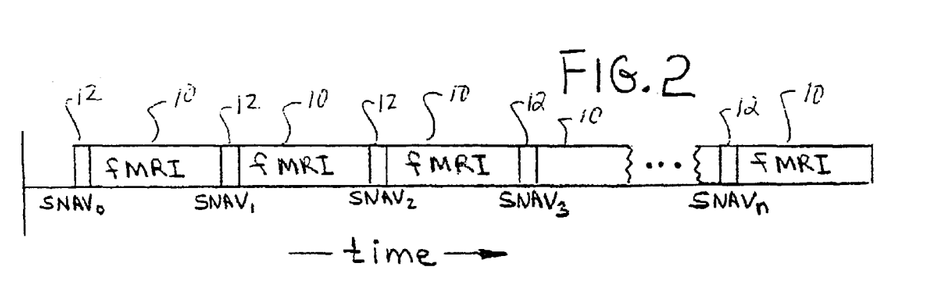
FIG. 2 is a graphic representation of an fMRI study which employs the present invention.

Referring particularly to FIG. 2, the preferred embodiment of the invention is employed in an fMRI study in which a series of image frames 10 are acquired over a 4 to 6 minute time. The present invention is practiced by interleaving a set of spherical navigator pulse sequences 12 between the successive set of fMRI frames 10. These are designated $SNAV_0$ through $SNAV_n$, where $SNAV_0$ records patient position at the beginning of the scan and which is referred to hereinafter as the reference position. A spherical navigator NMR signal is thus acquired just prior to each fMRI image frame, and its patient position information may be used to prospectively alter scan parameters to correct for the motion, or it may be used to retrospectively correct the fMRI image frame at the completion of the scan.

Figure 3:
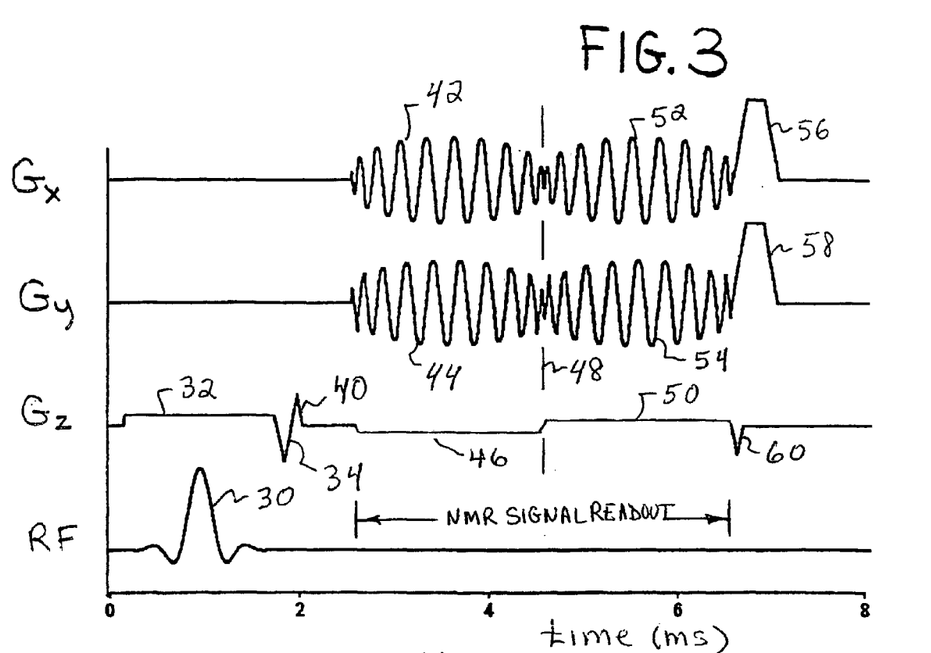
FIG. 3 is a graphic representation of a preferred embodiment of the spherical navigator pulse sequence of the present invention.
Figure 4:
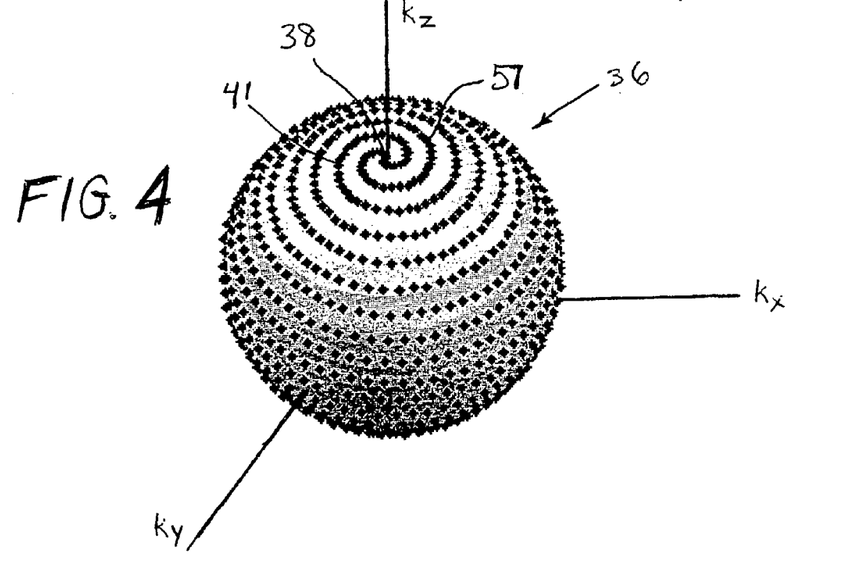
FIG. 4 is a graphic representation of the spherical sampling of k-space performed by the pulse sequence of FIG. 3.

Referring particularly to FIGS. 3 and 4, the spherical navigator pulse sequence includes a volume selective 30° RF excitation pulse 30 which is produced in the presence of a small $G_z$ slab select gradient pulse 32 to produce transverse magnetization throughout the region being imaged. For example, if ten slices are acquired during each fMRI image frame, the excited slab includes all ten slices. This is followed by a $G_z$ rephasing pulse 34 which has one-half of the area of $G_z$ slab select gradient pulse 32. the three gradient fields $G_x$, $G_y$ and $G_z$ are then manipulated during signal readout to sample three-dimensional k-space on the surface of a sphere 36 centered at the origin of k-space and having a radius $K_\rho = 9.5$.

In the preferred embodiment the spherical surface 36 is sampled by a spiral trajectory which starts at a point 38 where $k_z = k_\rho$, spirals down to the opposite side, or pole, of the sphere where $k_z = -k\rho$, and then spirals back to the starting point 38. The starting point is established by a $G_z$ dephasing gradient pulse 40, and the downward spiral sampling trajectory 41 is produced by sinusoidal $G_x$ and $G_y$ readout gradients in the presence of a small amplitude, negative $G_z$ gradient 46. The spiral sampling trajectory reverses direction at the time indicated by dashed line 48 and the $G_z$ gradient switches to a positive value 50. The $G_x$ and $G_y$ readout gradients 52 and 54 vary sinusoidally to produce a spiral sampling pattern 57 back to the starting point 38. The two spiral sampling patterns 41 and 57 are interleaved such that the surface of the sphere 36 is sampled substantially uniformly throughout. A total of 1952 samples of the NMR navigator signals are acquired during the signal readout. The equations for the three readout gradients during the readout period are as follows:

| Physical Parameters | | |
|---|---|---|
| Symbol | Description | Value |
| $\gamma/2\pi$ | gyromagnetic ratio | 4257 [Hz/Gauss] |
| $\Delta t$ | gradient time step | 4e-6 [sec] |
| M | time samples between k-space positions | 2 |
| N | number of k-space samples | 1008 |
| $k_\rho$ | k-space radius | 0.396 [cm$^{-1}$] |
| $S_{MAX}$ | max slew rate | 12,000 [Gauss/cm/sec] |
| $G_{MAX}$ | max gradient strength | 4 [Gauss/cm] |

| PHYSICAL EQUATIONS | | | |
|---|---|---|---|
| \multicolumn{4}{c}{Given a k-space trajectory: $\vec{k}(t)$} | | | |
| Gradient Waveforms | | $\vec{G}(t) = \dfrac{2\pi}{\gamma} \dfrac{d}{dt}\vec{k}(t)$ | (1) |
| Slew Rate | | $\vec{S}(t) = \dfrac{d}{dt}\vec{G}(t)$ | (2) |
| Continuous Time for Gradient | | $t = nM\Delta t = 2n\Delta t$ | (3) |
| \multicolumn{4}{c}{Pole-to-Pole Trajectory (T is Number of turns around the sphere)} | | | |
| Latitude | $\phi(n)$ | $\dfrac{\pi n}{N}$ | (4) |
| Longitude | $\theta(n)$ | $\dfrac{2\pi n T}{N}$ | (5) |
| k-space trajectory | $k_z$ | $k_\rho \cos\phi$ | (6) |
| | $k_x$ | $k_\rho \sin\phi \cos\theta$ | (7) |
| | $k_y$ | $k_\rho \sin\phi \sin\theta$ | (8) |
| Gradient waveforms | $G_z$ | $\dfrac{2\pi}{\gamma} \dfrac{d}{dt}\cos\left(\dfrac{\pi t}{2\Delta t \cdot N}\right)$ | (9) |
| | $G_x$ | $\dfrac{2\pi}{\gamma} \dfrac{d}{dt}\sin\left(\dfrac{\pi t}{2\Delta t \cdot N}\right)\cos\left(\dfrac{2\pi t T}{2\Delta t \cdot N}\right)$ | (10) |
| | $G_y$ | $\dfrac{2\pi}{\gamma} \dfrac{d}{dt}\sin\left(\dfrac{\pi t}{2\Delta t \cdot N}\right)\sin\left(\dfrac{2\pi t T}{2\Delta t \cdot N}\right)$ | (11) |
| \multicolumn{4}{c}{Equator-to-Pole Trajectory} | | | |
| k-space trajectory | $k_z(n)$ | $\dfrac{2n - N - 1}{N}$ | (12) |
| | $k_x(n)$ | $\cos\left(\sqrt{N\pi}\,\sin^{-1} k_z(n)\right)\sqrt{1 - k_z^2(n)}$ | (13) |
| | $k_y(n)$ | $\sin\left(\sqrt{N\pi}\,\sin^{-1} k_z(n)\right)\sqrt{1 - k_z^2(n)}$ | (14) |
| Gradient waveforms | $G_z(n)$ | $\dfrac{2\pi}{\gamma} \dfrac{d}{dt}\left(\dfrac{\frac{t}{\Delta t} - N - 1}{N}\right)$ | (15) |
| | $G_x(n)$ | $\dfrac{2\pi}{\gamma} \dfrac{d}{dt}\left(\cos\left(\sqrt{N\pi}\,\sin^{-1}\left(\dfrac{\frac{t}{\Delta t} - N - 1}{N}\right)\right)\sqrt{1 - \left(\dfrac{\frac{t}{\Delta t} - N - 1}{N}\right)^2}\right)$ | (16) |
| | $G_y(n)$ | $\dfrac{2\pi}{\gamma} \dfrac{d}{dt}\left(\sin\left(\sqrt{N\pi}\,\sin^{-1}\left(\dfrac{\frac{t}{\Delta t} - N - 1}{N}\right)\right)\sqrt{1 - \left(\dfrac{\frac{t}{\Delta t} - N - 1}{N}\right)^2}\right)$ | (17) |

Notice that the trajectory in $k_z$, i.e. from north pole to south pole is not linear. $B_0$ field inhomogeneity in the physical z direction will produce an apparent (false) z translation. Our solution to this problem is to describe a north-to-south-to-north pole or V-shaped $k_z$ trajectory rather than a linear pole-to-pole $k_z$ trajectory, so that a phase role in $k_z$ due to $B_0$ inhomogeneities can be distinguished from actual physical translation of the object in $k_z$.

After the navigator signal readout is complete $G_x$ and $G_y$ spoiler gradient pulses 56 and 58 are applied. A negative $G_z$ rewinder gradient pulse 60 is also applied. These gradients prepare the spin magnetization for the fMRI pulse sequence which immediately follows:

While it is preferred to sample the entire surface of k-space sphere 36, good results have also been obtained by sampling less than the entire surface. More specifically, the ability of the MRI system gradient amplifiers 127 to slew the $G_x$ and $G_y$ readout gradient at a sufficiently high rate to produce the above-described spiral trajectory pattern may limit the ability to sample near the "poles" of the sphere 36 where the sampling pattern spirals more quickly. It has been discovered that up to 15% of the surface can be unsampled without significantly affecting the motion measuring accuracy of the acquired NMR navigator signal. In this case it may be advantageous to sample the spherical surface 36 in two separate excitations. During the first excitation the upper half of the spherical surface 36 is sampled by starting at the "equator" (i.e. $k_z=0$) and spiraling upward toward the north pole (i.e. $k_z=+k_\rho$) until the maximum slew rate of the gradient system is reached. This is followed by a second excitation in which the lower half of the spherical surface 36 is sampled by spirally downward from the equator toward the south pole ($k_z=-k_\rho$). A total of 1008 samples are acquired during each of these two readouts in this alternative embodiment of the invention.

The processing of the SNAV signals may either be done in real time if prospective motion correction is to be performed, or it may be done after the scan is complete if retrospective correction of the acquired fMRI data is to be performed.

Figure 5:
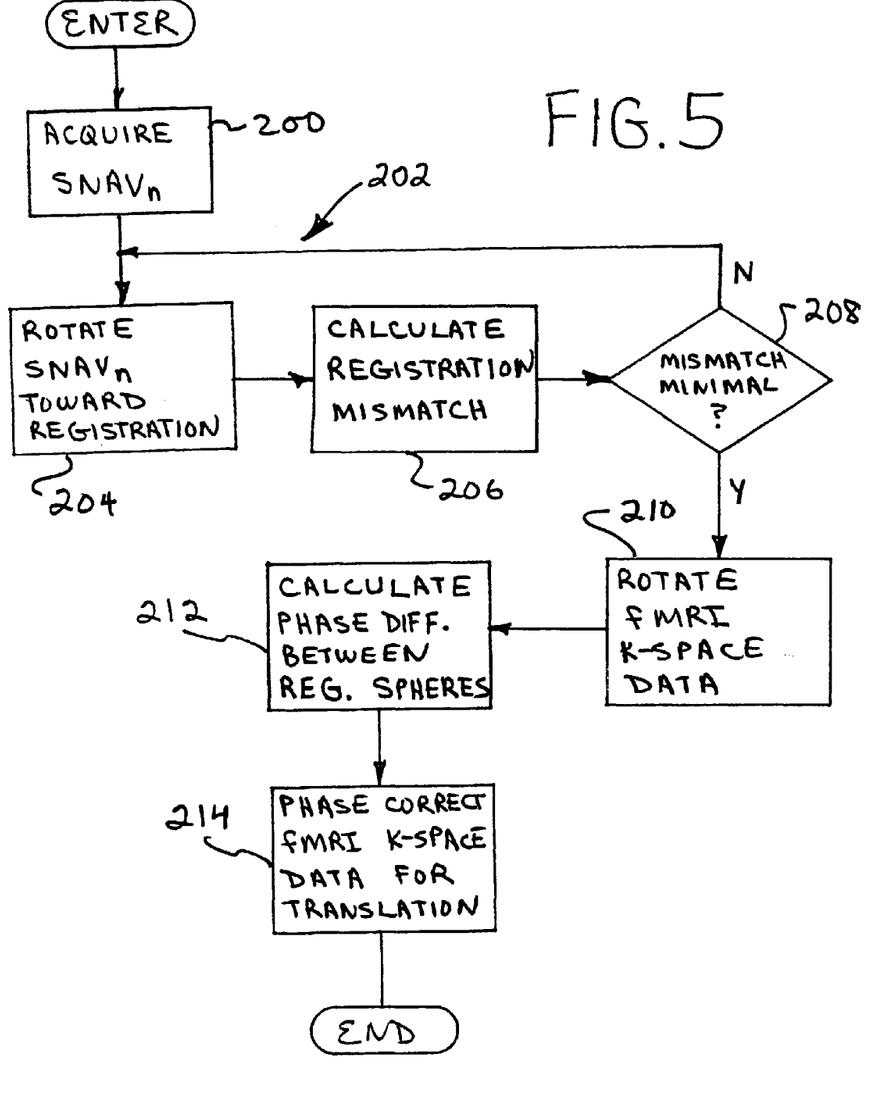
FIG. 5 is a flow chart of the method used to correct image data with navigator signals acquired with the pulse sequence of FIG. 3.

Referring particularly to FIG. 5, the $SNAV_n$ signal is acquired for the fMRI k-space data set to be motion corrected as indicated at process block 200 and described above. This is a retrospective correction of fMRI data (i.e. correction after the data is acquired). However, it can be appreciated by those skilled in the art that a prospective correction of the fMRI image frame, as well as prospective or retrospective correction of each view-to-view motion or block-to-block motion may also be performed using the present invention. A loop is entered at 202 in which the acquired spherical navigator k-space data $SNAV_n$ is rotated until it reaches optimum registration with the reference spherical navigator $SNAV_0$. This is illustrated in the texture maps of FIGS. 7b and 7c which illustrate by their shading the magnitude values on the k-space sphere. We perform this registration by minimizing a cost function that measures the degree of mismatch between the reference spherical navigator ($SNAV_0$) data set and the acquired ($SNAV_n$) data set as trial rotations are applied to the latter. Initial experiments were performed using the sum squared difference as the cost function and downhill simplex minimization as the optimization algorithm as described by Press et al. "Numerical Recipes in C," $2^{nd}$ ed. New York, N. Y.: Cambridge University Press (1992). All three rotation angles ($\theta_x$, $\theta_y$, $\theta_z$) are solved for simultaneously by the algorithm, which typically requires 20–50 iterations to converge.

Each trial rotation of $SNAV_n$ is performed at process block 204 and the mismatch between it and the reference navigator signal $SNAV_0$ is calculated at process block 206. For each sample point of $SNAV_n$, its $\theta$ and $\phi$ coordinates after the rotation are calculated. The corresponding magnitude value for $SNAV_0$ is calculated using bilinear interpolation of the four sample points that surround these coordinates in $\theta$ and $\phi$. The squared difference between the interpolated magnitude value from the reference data $SNAV_0$ and the measured value from the acquired/rotated data is calculated. The sum of these squared differences for all the sample points on the k-space sphere is the cost function value for the iteration.

When the mismatch is minimized, as indicated at decision block 208, the registration is complete. Otherwise, the system loops back to try another set of rotation angles. As indicated at process block 210 the correction angles which register the two spherical data sets $SNAV_0$ and $SNAV_n$ are then used to correct the associated fMRI k-space data set. This is accomplished by rotating the entire fMRI k-space data set about the origin of k-space using the rotation angles $\theta_x$, $\theta_y$, $\theta_z$. This corrects the fMRI data for patient rotation about any axis in space.

The next step as indicated by process block 212 is to calculate the phase difference at each sample point in the two registered k-space spheres. Transitional motion does not alter magnitude values on the spherical shell, but does alter phase values. At each point in 3-D k-space, a translation of ($\Delta_x$, $\Delta_y$, $\Delta_z$) causes a phase change $\Delta\phi$ according to equation (18). If the spherical shell is sampled with N points, then each point yields an equation of this form, building a system of N equations in 3 unknowns. The calculation $$\Delta\phi = 2\pi[\Delta x k_x + \Delta y k_y + \Delta z k_z]. \tag{18}$$

of translation is thus highly over determined and is expected to be quite robust. Note that the general process of determining translations after a rotation requires regridding of the points from the original to the rotated grid, which involves the calculation of phase values from interpolated data. Once the phase values are registered by any necessary rotation, the unwrapped phase differences can be plugged into a weighted least squares inversion to find the ($\Delta_x$, $\Delta_y$, $\Delta_z$) translation. Equations (19–22) below describe the weighted least squares inversion calculation. The 3×1 column vector x contains the unknown motions. The elements of the N×1 column vector b are the unwrapped phase differences. The rows of the N×3 matrix A contain the (kx, ky, kz) position of each sampled point in k-space. The N×N weighting matrix W has been added in equation (19) to account for higher noise in the phase at low magnitude positions in k-space. After calculating the inverse of the 3×3 matrix Q defined in equation (21), one can find the best least squares fit ($\Delta_x$, $\Delta_y$, $\Delta_z$) translations in x using equation (22).

$$Ax = b \tag{19}$$

$$(A^T W A)x = A^T W b \tag{20}$$

$$Q = A^T W A \tag{21}$$

$$x = Q^{-1} A^T W b \tag{22}$$

The fMRI data set is thus corrected for patient rotation in any direction and for translational motion in any direction. It can be appreciated that while the present invention has particular application to fMRI, it also has application to other clinical situations in which complex three-dimensional movement of the subject is a problem. For example, in cardiac imaging the heart moves in a complex pattern during each cardiac cycle. In this case, spherical navigator pulse sequences may be interleaved between individual imaging pulse sequences or sets of imaging pulse sequences rather than entire image frames as described above.

The invention claimed is:

1. A method for detecting movement of a subject during a scan in which NMR image data is acquired with a magnetic resonance imaging system, the steps comprising:
   a) acquiring the NMR image data using a series of NMR imaging pulse sequences;
   b) interleaving with the series of NMR imaging pulse sequences a series of NMR navigator signal pulse sequences, each navigator signal pulse sequence including the application of three orthogonal magnetic field gradients during the readout of its NMR navigator signal such that a resulting NMR navigator signal samples a three-dimensional surface in k-space;
   c) acquiring the NMR navigator signals during the scan; and
   d) analyzing the acquired NMR navigator signals to measure rotational and translational motion of the subject during the scan;
   e) calculating corrective values from the measured subject rotation and subject translation; and
   f) correcting NMR image data using the corrective values.

2. The method as recited in claim 1 in which the three-dimensional surface is substantially spherical in shape.

3. The method as recited in claim 1 in which the three-dimensional surface is substantially hemispherical in shape.

4. The method as recited in claim 2 in which the spherical surface is centered around the origin of k-space.

5. The method as recited in claim 1 in which step d) includes:
   i) registering an acquired NMR navigator signal with a reference NMR navigator signal to determine rotation of the subject; and
   ii) determining the phase difference between the registered acquired NMR navigator signal and the reference NMR navigator signal to determine translation of the subject.

6. The method as recited in claim 1 in which the NMR image data is corrected after its acquisition.

7. The method as recited in claim 1 in which two of the magnetic field gradients applied during the navigator signal pulse sequence vary sinusoidally during the readout of its navigator signal to produce a spiral sampling trajectory.

8. The method as recited in claim 7 in which the third magnetic field gradient applied during the navigator signal pulse sequence varies such that the spiral sampling trajectory defines at least a portion of a substantially spherical three-dimensional surface.

9. The method as recited in claim 8 in which the portion is at least 85% of a spherical surface.

10. The method as recited in claim 1 in which 1000 to 2000 samples of said three-dimensional surface in k-space are acquired by the navigator signal.

11. The method as recited in claim 1 in which the NMR image data is corrected prior to its acquisition.

12. The method as recited in claim 1 in which the NMR image data acquired in step a) is processed by reconstructing a time series of images; and in which the NMR navigator signal pulse sequence is performed prior to the acquisition of NMR image data for each of the reconstructed images.

13. A method for acquiring fMRI data from a subject with a magnetic resonance imaging (MRI) system, the steps comprising:
   a) acquiring NMR image data by performing a series of NMR imaging pulse sequences with the MRI system;
   b) forming the acquired NMR image data into a series of data sets from which a corresponding series of images may be reconstructed;
   c) interleaving with the series of NMR imaging pulse sequences a series NMR navigator signal pulse sequences, each navigator signal pulse sequence being associated with a data set and including the application of three orthogonal magnetic field gradients during the readout of its NMR navigator signal such that a resulting NMR navigator signal samples a portion of a substantially three-dimensional spherical surface in k-space;
   d) acquiring each NMR navigator signal and with respect to each:
      i) analyzing the NMR navigator signal to measure motion of the subject;
      ii) calculating corrective values from the measured subject motion; and
      iii) correcting the NMR image data in its associated data set using the corrective values.

14. The method as recited in claim 13 in which step d)i) includes:
   registering the NMR navigator signal with a reference NMR navigator signal to determine rotation of the subject; and
   determining the phase difference between the registered NMR navigator signal and the reference NMR navigator signal to determine translation of the subject.

* * * * *